United States Patent
Biba et al.

(10) Patent No.: US 10,744,292 B2
(45) Date of Patent: Aug. 18, 2020

(54) APPARATUS AND METHOD FOR FILTERING LIQUID PARTICLES FROM INSPIRATORY GAS FLOW OF A PATIENT BREATHING CIRCUIT AFFILIATED WITH A VENTILATOR AND/OR NITRIC OXIDE DELIVERY SYSTEM

(71) Applicant: Mallinckrodt Hospital Products IP Limited, Dublin (IE)

(72) Inventors: Scott I. Biba, Waunakee, WI (US); John Falligant, Edgerton, WI (US)

(73) Assignee: Mallinckrodt Hospital Products IP Limited, Dublin (IE)

( * ) Notice: Subject to any disclaimer, the term of this patent is extended or adjusted under 35 U.S.C. 154(b) by 418 days.

(21) Appl. No.: 15/446,110

(22) Filed: Mar. 1, 2017

(65) Prior Publication Data

US 2017/0281896 A1    Oct. 5, 2017

Related U.S. Application Data

(60) Provisional application No. 62/316,663, filed on Apr. 1, 2016.

(51) Int. Cl.
*B01D 53/22* (2006.01)
*A61M 16/08* (2006.01)
(Continued)

(52) U.S. Cl.
CPC ...... *A61M 16/0808* (2013.01); *A61M 16/085* (2014.02); *A61M 16/105* (2013.01);
(Continued)

(58) Field of Classification Search
CPC ............ B01D 46/0023; B01D 2277/20; B01D 46/10; B01D 46/4254; B01D 46/0031;
(Continued)

(56) References Cited

U.S. PATENT DOCUMENTS 2,521,785 A * 9/1950 Goodloe ............ B01D 46/0023
  55/482
3,458,050 A * 7/1969 Cooper ................. B01D 35/02
  210/448

(Continued)

FOREIGN PATENT DOCUMENTS

WO    2000032295 A2    6/2000
WO    2006091594 A1    8/2006

OTHER PUBLICATIONS

"Density" The American Heritage Dictionary of the English Language, Fourth Edition copyright 2000 by Houghton Mifflin Company. Updated in 2009. 1 page. https://web.archive.org/web/20120201043247/https://www.thefreedictionary.com/density (Year: 2009).*

(Continued)

*Primary Examiner* — Anthony R Shumate

(57) ABSTRACT

The present disclosure relates to a filter apparatus for filtering liquid from a gas, the apparatus having a first housing having a gas inlet and a gas outlet; a first filter media disposed in the first housing; a second filter media disposed in the housing; and a second housing forming a first collection basin disposed in the flow path between the first filter media and the second filter media, so that a path is defined for the gas flowing from the inlet, through the first filter media, past the collection basin, through the second filter media, and to the outlet. The present disclosure also relates to a method of passing a gas through a coalescing filter media and through a hydrophobic filter media.

16 Claims, 5 Drawing Sheets

(51) Int. Cl.
*A61M 16/10* (2006.01)
*B01D 46/00* (2006.01)
*B01D 46/10* (2006.01)
*B01D 46/42* (2006.01)

(52) U.S. Cl.
CPC ..... *B01D 46/0023* (2013.01); *B01D 46/0031* (2013.01); *B01D 46/10* (2013.01); *B01D 46/4254* (2013.01); *A61M 2205/3303* (2013.01); *A61M 2205/581* (2013.01); *A61M 2205/583* (2013.01); *A61M 2205/7536* (2013.01); *A61M 2230/437* (2013.01); *B01D 2277/20* (2013.01)

(58) Field of Classification Search
CPC .. A61M 2205/7536; A61M 2205/3303; A61M 2230/437; A61M 16/105; A61M 16/0808; A61M 2205/583; A61M 2205/581; A61M 16/085
See application file for complete search history.

(56) References Cited

U.S. PATENT DOCUMENTS

| | | | | |
|---|---|---|---|---|
| 3,910,998 | A * | 10/1975 | Vamashita | C07C 51/42 562/485 |
| 4,138,591 | A * | 2/1979 | Baur | C07C 37/14 568/756 |
| 4,273,938 | A * | 6/1981 | Merger | C07C 231/06 564/124 |
| 4,366,131 | A * | 12/1982 | Fox | B01D 53/52 423/231 |
| 4,487,618 | A * | 12/1984 | Mann | B01D 46/0012 55/323 |
| 4,613,369 | A * | 9/1986 | Koehler | B01D 39/12 419/2 |
| 4,874,408 | A * | 10/1989 | Overby | B01D 5/009 96/408 |
| 5,098,729 | A * | 3/1992 | Engel | A23J 3/10 426/330.2 |
| 5,368,021 | A | 11/1994 | Beard et al. | |
| 5,826,575 | A | 10/1998 | Lall | |
| 6,007,608 | A | 12/1999 | Johnson | |
| 6,210,469 | B1 * | 4/2001 | Tokar | A47L 9/102 55/319 |
| 6,305,913 | B1 * | 10/2001 | Hashish | A23L 3/0155 417/392 |
| 6,773,589 | B2 * | 8/2004 | Sharkey | B01D 21/02 210/269 |
| 7,879,062 | B2 * | 2/2011 | Galdonik | A61F 2/01 606/200 |
| 2002/0116910 | A1 | 8/2002 | Berger et al. | |
| 2006/0130883 | A1 * | 6/2006 | Niedzwiecki | B08B 3/026 134/94.1 |
| 2007/0204924 | A1 * | 9/2007 | Delgiacco | F16K 3/085 137/625.31 |
| 2007/0277485 | A1 * | 12/2007 | MacKenzie | B01D 45/08 55/424 |
| 2009/0013873 | A1 | 1/2009 | Larsen et al. | |
| 2010/0307341 | A1 | 9/2010 | Peter et al. | |
| 2011/0067699 | A1 | 3/2011 | Caruso et al. | |
| 2011/0147299 | A1 * | 6/2011 | Stanfel | B01D 17/045 210/491 |
| 2012/0136269 | A1 | 5/2012 | Weckstrom | |
| 2012/0211411 | A1 * | 8/2012 | Hopkins | B01D 29/111 210/333.01 |
| 2014/0044600 | A1 * | 2/2014 | McAlister | B01J 19/087 422/128 |
| 2014/0246365 | A1 * | 9/2014 | McPeak | B01D 24/22 210/167.01 |
| 2014/0250845 | A1 * | 9/2014 | Jackson | B01D 46/0005 55/484 |
| 2014/0311963 | A1 * | 10/2014 | Bortnik | B01D 36/003 210/335 |
| 2015/0292455 | A1 | 10/2015 | Metz et al. | |
| 2016/0031733 | A1 * | 2/2016 | Scheurer | C02F 1/72 210/758 |
| 2016/0051747 | A1 * | 2/2016 | Wegener | A61M 1/0209 435/325 |
| 2017/0144128 | A1 * | 5/2017 | Carrion | B01J 19/14 |

OTHER PUBLICATIONS

Perry et al. "Perrys Chemical Engineers handbook" The McGraw-Hill Companies, Inc. 1999, p. 22-37 (Year: 1999).*
European Search Report regarding European application No. 17776200.2, 7 pages.

* cited by examiner

APPARATUS AND METHOD FOR FILTERING LIQUID PARTICLES FROM INSPIRATORY GAS FLOW OF A PATIENT BREATHING CIRCUIT AFFILIATED WITH A VENTILATOR AND/OR NITRIC OXIDE DELIVERY SYSTEM

CROSS-REFERENCE TO RELATED APPLICATIONS

This application claims priority to U.S. patent application Ser. No. 62/316,663, filed on Apr. 1, 2016 and entitled "APPARATUS AND METHOD FOR FILTERING LIQUID PARTICLES FROM INSPIRATORY GAS FLOW OF A PATIENT BREATHING CIRCUIT AFFILIATED WITH A VENTILATOR AND/OR NITRIC OXIDE DELIVERY SYSTEM," the contents of which are incorporated herein by reference in their entirety.

FIELD

The present disclosure generally relates to the filtration or separation of liquid particles from sampled inspiratory gas flow of a patient breathing circuit affiliated with a ventilator and/or therapeutic gas delivery system (e.g., inhaled nitric oxide gas delivery system).

BACKGROUND

Many patients benefit from receiving therapeutic gas (e.g., nitric oxide gas) in inspiratory breathing gas flow from a breathing circuit affiliated with a ventilator (e.g., constant flow ventilator, variable flow ventilator, high frequency ventilator, bi-level positive airway pressure ventilator or BiPAP ventilator, etc.). To provide therapeutic gas to a patient who receives breathing gas from a ventilator, the therapeutic gas may be injected into the inspiratory breathing gas flowing in the breathing circuit. This inhaled therapeutic gas is often provided via a therapeutic gas delivery system as a constant concentration, which is provided based on proportional delivery of the therapeutic gas to the breathing gas. Further, a sampling system (e.g., affiliated the therapeutic gas delivery system) may continuously draw in the inspiratory breathing gas flow to at least confirm that the desired dose of the therapeutic gas in the inspiratory breathing gas flow is being delivered to the patient. For example, a sample pump may pull in inspiratory flow (e.g., in the near vicinity of the patient) to confirm that the desired therapeutic gas concentration is in fact being delivered to the patient in need thereof.

One such therapeutic gas is inhaled nitric oxide (iNO). In many instances iNO is used as a therapeutic gas to produce vasodilatory effect on patients. When inhaled, nitric oxide (NO) acts to dilate blood vessels in the lungs, improving oxygenation of the blood and reducing pulmonary hypertension. Because of this, nitric oxide is provided in inspiratory breathing gases for patients with various pulmonary pathologies including hypoxic respiratory failure (HRF) and persistent pulmonary hypertension (PPH). The actual administration of iNO is generally carried out by its introduction into the patient as a gas along with other normal inhalation gases, for example, by introducing iNO, from an iNO delivery system, into the inspiratory flow of a patient breathing circuit affiliated with a ventilator.

Separately and/or in conjunction with iNO, patients may receive inspiratory breathing gas flow containing liquid particles (e.g., nebulized medical solutions and suspensions, moisture from humidified air, etc.) and/or other particles. Although this matter in the inspiratory breathing flow may provide additional benefit to the patient, they may contaminate the sampling system (e.g., gas analyzers) of the therapeutic gas delivery system used to confirm dosing of iNO being delivered to the patient. Unlike the mere filtering of liquids from gas, filtering these contaminates from the sampled inspiratory breathing gas flow can be substantially difficult. Filtration design complexities or difficulties may include the desire for very low internal and external leakage, very low resistance to flow, and materials compatibility such that filter materials used do not adulterate the gas sample to be analyzed. Low internal and external leakages are critical in this application, as nitric oxide (NO) is monitored in the range of 1 to 80 parts per million (ppm) and nitrogen dioxide (NO2) in the range of 1 to 5 ppm. A small external leak, for example, may dilute the sample to be analyzed, potentially rendering inaccurate sample gas analysis. A small internal leak may allow contaminant to pass through the filter, resulting in potential performance degradation of downstream pneumatic controls and/or gas analyzer sensors, also having the potential of rendering inaccurate sample gas analysis. Low filter resistance to flow is critical as this attribute relates directly to pump power requirements. Lower resistance to flow enables smaller pumps consuming less power to be used, resulting in smaller, lighter, quieter medical devices. The impact of lower power components can be compounded for devices requiring battery back-up, allowing for use of smaller batteries. Medical device pumps operating at lower sound pressure levels can be especially advantageous in settings such as the ICU, where quiet operation is critical to the clinical staff. Other competing physical attributes from User's perspective are desire for longevity (e.g., infrequent filter changes would come with larger filters) in contrast with desire for compact device (which may require smaller filters). Adding complexity, the sampled inspiratory flow is typically required throughout treatment (e.g., constant or near constantly sampling of the inspiratory flow just prior to, in the immediate vicinity of, entry into the patient) to provide real time, or near real time, confirmation of dosing during therapeutic gas delivery to the patient.

Accordingly, at times, there is a need to filter the sampled inspiratory breathing gas flow of liquid particles and/or other particles, for example, to mitigate contamination of the gas sampling system. Further, there may also be other uses for an improved apparatus and method that can effectively filter at least these, or other, contaminants from sampled inspiratory breathing gas flow being provided to a patient in need thereof.

SUMMARY

Generally speaking, aspects of the present disclosure relate to filtration apparatuses and methods to remove liquid particles from a gas stream containing humidity, water vapor, nebulized liquid or other liquid components. Particulates may also be removed. More specifically, aspects of the present disclosure relate to filtration devices and methods to remove liquid particles and/or particles from sampled inspiratory gas flow of a patient breathing circuit affiliated with a ventilator and/or therapeutic gas delivery system (e.g., inhaled nitric oxide gas delivery system). The removal of these liquid particles and/or particles is needed as they can contaminate the sampling system affiliated with the therapeutic gas delivery system.

In exemplary implementations of the present disclosure there is provided a filter apparatus for filtering liquid from a gas, comprising: a housing having a gas inlet and a gas outlet; a first filter media disposed in the housing; a second filter media disposed in the housing; and a first collection basin disposed in the flow path between the first filter media and the second filter media, wherein a path is defined for the gas flowing from the inlet, through the first filter media, past the collection basin, through the second filter media, and to the outlet.

In at least some aspects of the present disclosure, the first filter media may be a coalescing media. The second filter media may be a hydrophobic media. The first filter media and the second filter media may be both mounted to, or otherwise integral to, the housing. The filtration pore size of the first filter media may be greater compared with the pore size (which also may be referred to in terms of degree of coarseness or fineness) of the second filter media. The first filter media may be configured so that droplets of liquid collected by the first filter media may fall (e.g., as droplets via gravity) into the first collection basin. The second filter media may be configured so that droplets of liquid collected by the second filter media may fall (e.g., as droplets via gravity) into the first collection basin. The housing may further comprise a second collection basin, wherein droplets of liquid collected by the second filter media may fall (e.g., as droplets via gravity) into the second collection basin. At least some aspects of first and/or second collection basin may be defined by the housing and/or the second collection basin may be separate from the first collection basin. In at least some instances the first and/or second collection basin may be defined by the housing, the second collection basin can be separate from the first collection basin. Further, in at least some instance the first and/or second collection basin may not be defined by the housing. In at least some instances, the second collection basin may not be separate from the first collection basin.

In at least some aspects of the present disclosure, the filtration density of the first filter media may be approximately 1 micron, the filtration density of the first filter media may be approximately [1] micron to [5] micron, the filtration density of the second filter media may be approximately 0.2 microns, and/or the filtration density of the second filter media may be approximately [0.1] micron to [0.3] micron. The first filtration media and the second filtration media may be arranged at a non-zero angle relative to each other (e.g., oblique, perpendicular, skewed, etc.), or arranged parallel to each other. The filter media should be oriented such that the combination of gravity and gas flow (through the media) encourages shedding of droplets into collection basin. A vertical orientation may be preferred when compared with horizontal, strictly from a gravitational shedding perspective, but other orientations (e.g., vertical +/−45 degrees) would also be successful at shedding liquid droplets in combination with gas flow through the media, and would increase design flexibility.

In at least some aspects of the present disclosure, the housing defines a first aperture below the first filter media, and a second aperture below the second filter media, with the first and second apertures sized so that liquid drops fall though the apertures, but splashing from the basin to the second media is inhibited.

In other aspects, the first filter media comprises a fiberglass material, and/or the second filter media comprises an expanded PTFE material. The area of the first filter media may be larger when compared with the second filter media, as the first filter media will capture most of the contaminants entering [such as inorganic materials (e.g., salts from saline which may be nebulized directly or indirectly as diluent of other nebulized medications), or organic materials (e.g., complex hydrocarbon nebulized medications)] whereas the second filter would be a further filtration refinement of same.

In another exemplary implementation of the present disclosure, a filter apparatus for filtering liquid from a gas is provided, comprising: a first housing having a gas inlet and a gas outlet; a first filter media disposed in the first housing; a second filter media disposed in the second housing; and a second housing forming a first collection basin disposed in the flow path between the first filter media and the second filter media, wherein a path is defined for the gas flowing from the inlet, through the first filter media, past the collection basin, through the second filter media, and to the outlet.

In another example of implementations, a method of filtering liquid from a gas, comprises passing the gas through a coalescing filter media; collecting liquid filtered by the coalescing filter media to form a first-filtered gas; passing the first-filtered gas through a hydrophobic filter media to form a second-filtered gas; and collecting liquid filtered by the hydrophobic media.

Other features and aspects of the disclosure will be apparent from the following detailed description, the drawings, and the claims.

BRIEF DESCRIPTION OF THE DRAWINGS

The features and advantages of the present disclosure will be more fully understood with reference to the following, detailed description when taken in conjunction with the accompanying figures, wherein.

DETAILED DESCRIPTION

The present disclosure generally relates, to filtration of liquid from a gas containing the liquid. The liquid component may be any removable liquid, such as, for example, humidity, water vapor, moisture from humidified air, other liquids in a vapor state, nebulized liquids, nebulized medical solutions and suspensions, etc. In some implementations, the present disclosure describes apparatus and methods for such filtration in the context of delivery of therapeutic gas to patients (e.g., patients receiving breathing gas, which can include therapeutic gas, from a ventilator circuit), and further to implementations where a sample breathing gas is removed from an inspiratory limb to be monitored by a sampling device. This sampling device can be needed to continuously confirm at least dosing (e.g., nitric oxide concentration, etc.) as well as other parameters (e.g., nitrogen dioxide concentration, oxygen concentration, etc.). As discussed further herein, filters according to the present disclosure can be installed in between the source of breathing gas and the sampling device, which may reduce contamination, for example, improving operation and/or longevity of the sampling device.

The concept of filtering suspended or entrained water vapor or other liquid components before a sample gas reaches a sampling device may be referred to at times as a "water trap," or "filter trap." However, the present disclosure relates to some implementations that can remove more than just water, such as, for example, nebulized liquids which may be nebulized medications.

The terms liquid particles and/or particles are used herein in their broadest sense to encompass any and all of particles, liquid or solid, organic or inorganic, which could be in the gas flow such as, but not limited to, nebulized medical solutions and suspensions, aerosols, moisture from humidified air, or other contaminants present in patient breathing circuit resulting from treatments delivered via the breathing circuit. At times the term liquid particles, particles, matter, or the like are used individually or to refer to a common group of material to be removed.

The terms "filter" and "filtration" are used herein in their broadest sense to encompass any and all of various types and degrees of removal or separation of liquid from gas, and may also include removal of other non-liquid particulates if present in some cases.

Figure 1:
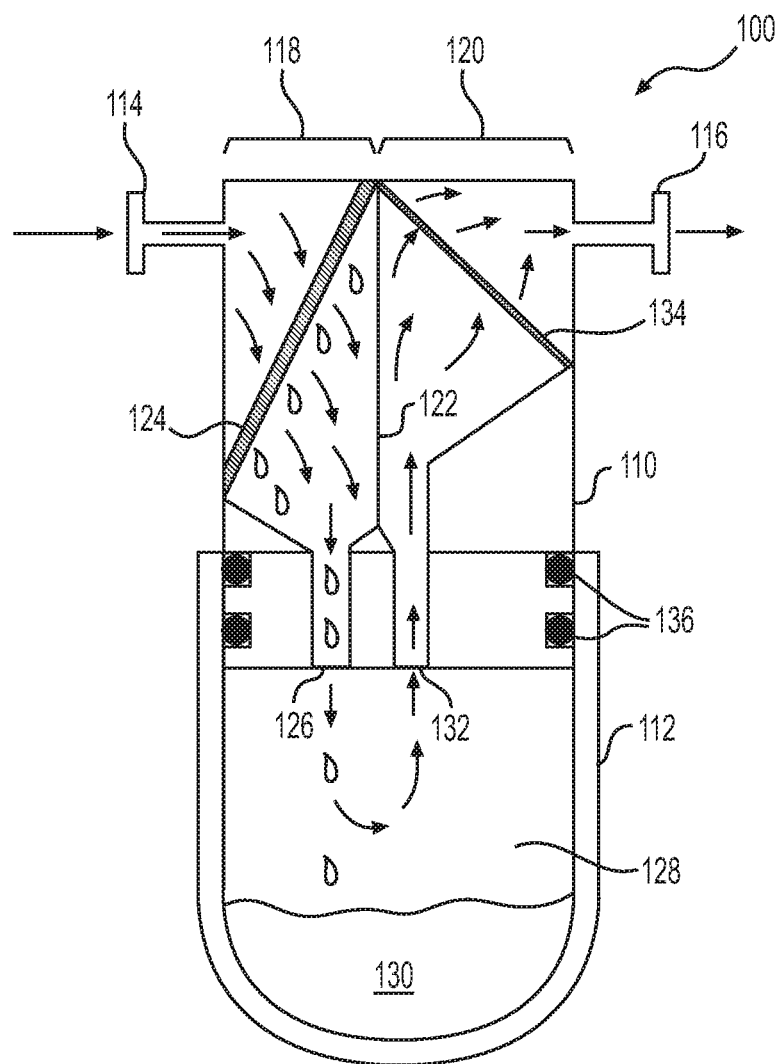
FIG. 1 illustratively depicts a cross section of an exemplary filter assembly according to an exemplary first implementation, in accordance with exemplary embodiments of the present disclosure.

FIG. 1 illustratively depicts a cross section of an exemplary filter assembly 100 according to an exemplary first implementation. An upper housing 110 is coupled with a lower housing 112. The upper housing 110 includes an inlet 114, which receives a flow of gas, which may, for example be sample gas taken from an inspiratory limb or other portion of a breathing gas device, as described in more detail below. The upper housing 110 also includes an outlet 116, from which filtered gas exits the filter assembly 100, and the outlet 116 may be connected to a downstream component of a breathing gas device such as a gas sampling system or gas analyzer, as described in more detail below.

The upper housing 110 may be referred to as housing and/or include a "first stage filtration portion" 118, which may also be referred to as a "coalescing filtration portion" 118, and a "second stage filtration portion" 120 which may also be referred to as a "hydrophobic filtration portion 120." The first stage filtration portion supports a coalescing filter media, or filter membrane 124 which may also be referred to as a first stage media 124.

The first stage media 124 may be adapted to remove a range of airborne entrained liquid from the gas. The first stage media 124 may also remove particulate matter. For example the first stage media 124 may, in some examples remove 1.0 micron or larger droplets or particulates. The first stage media 124 may, in some examples have a glass fiber type mesh construction creating a textured surface. As the gas passes through the first stage media 124, liquid droplets form in the mesh construction and collect on the textured surface. These droplets are drawn by gravity and/or other forces (e.g., negative pressure, gravity, etc.) to the back, lower side of the first stage media 124 and fall downward off the first stage media 124. The droplets may pass through a first channel or aperture 126 at a lower end of the upper housing 110, and fall into a collection basin 128 and into a pool 130.

The now first-stage-filtered gas is driven, for example, by pressure (e.g., pressure differential) upward through a second channel or aperture 132 into the second stage filtration portion 120. The first stage filtered gas now passes through a hydrophobic filter media 134, or filter membrane 134 which may also be referred to as a second stage media 134.

The second stage media 134 may also be adapted to remove a range of airborne entrained liquid from the gas, and may to some extent remove 0.2 micron or larger droplets or particulate matter. For example, the second stage media 134 may in some examples be a porous polytetrafluoroethylene (PTFE) material. As the gas flows through the second stage media 134 droplets and particulates will be blocked from passing through, and may simply fall via gravity and/or other forces (e.g., negative pressure, gravity, etc.) through the aperture 132 and join the pool 130. The gas that has passed through the second stage media 134 then exits the filter assembly 100 via the outlet 116.

It will be noted in this exemplary implementation, that the first stage media 124 may be referred to as being more coarse (less fine) than the second stage media 134. That is, the first stage media 124 may have a pore size that is larger than a pore size of the second stage media 134. The first stage media 124 may thus be, in some examples, considered a pre-filter for the second stage media 134. In so doing, the first stage media 124 may extend the useful lifespan of the second stage media 134, because the first stage media 124 removes droplets or particles that would effectively clog up or oversaturate, wet out or blind occlusion of the second stage media 134. In some implementations, the filtration density of the first filter media may be approximately 1 micron, and/or the filtration density of the first filter media may be approximately [1] micron to [5] microns, the filtration density of the second filter media may be approximately 0.2 microns, and/or the filtration density of the second filter media may be approximately [0.1] micron to [0.3] micron.

In this exemplary implementation, the second stage media 134 is also separated from the pool 130 by a vertical distance and by the size of the aperture 132. These features help avoid the likelihood of liquid in the pool 130 from splashing (e.g., during movement of the filter assembly 100) or evaporating towards the second stage media 134. This degree of enhanced separation of the pool 130 from the second stage media 134 also may extend the useful life of the second stage media 134. The pre-filtration by the first stage media 124 may also have the advantage of reducing the needed area and amount of material for the second stage media 134, compared to if the pre-filtration was not provided.

The first stage media 124 and second stage media 134 can each be mounted at their peripheries to the upper housing 110, so that all gas must pass through both media. Of course the first stage media 124 and second stage media 134 can each be mounted to the upper housing 110 at any location. At times, the first stage media 124 and second stage media 134 are depicted and/or described as being mounted at their peripheries to the upper housing. This is merely for ease and is in no way meant as a limitation. Mounting may be accomplished via various mounting and attachment methods such as gluing, mechanical connection into a groove, compression, heat welding, vibration welding, other welding, pre-molding or overmolding into the housing 110, and/or other attachments. The media 124 and 134 may have an overmolded outer structural support that is mechanically attached to the housing 110. Gaskets may also be overmolded or placed as part of the attachment to the housing 110. In some implementations, the design may focus on a stricter or tighter surrounding fit for the second stage media 134, for example, since this is the final desired filtration density.

The two stage implementation also provides for a first stage that may, in some implementations and situations, remove mostly water droplets, and a second stage that may primarily remove nebulized liquid such as a drug or saline that may be in the gas entering the filter assembly 100.

The lower housing 112 may be removably, in some implementations, attached or coupled to the upper housing 110. This may be a friction fit using elastomeric O-rings 136 as shown in FIG. 1. There may also be threading attaching the lower and upper housings 110 and 112. Removal of the lower housing 112 permits a user to empty the pooled content 130. The lower housing 112 may be transparent or translucent to assist the user in observing when to remove and empty the liquid lower housing 112.

Figure 2:
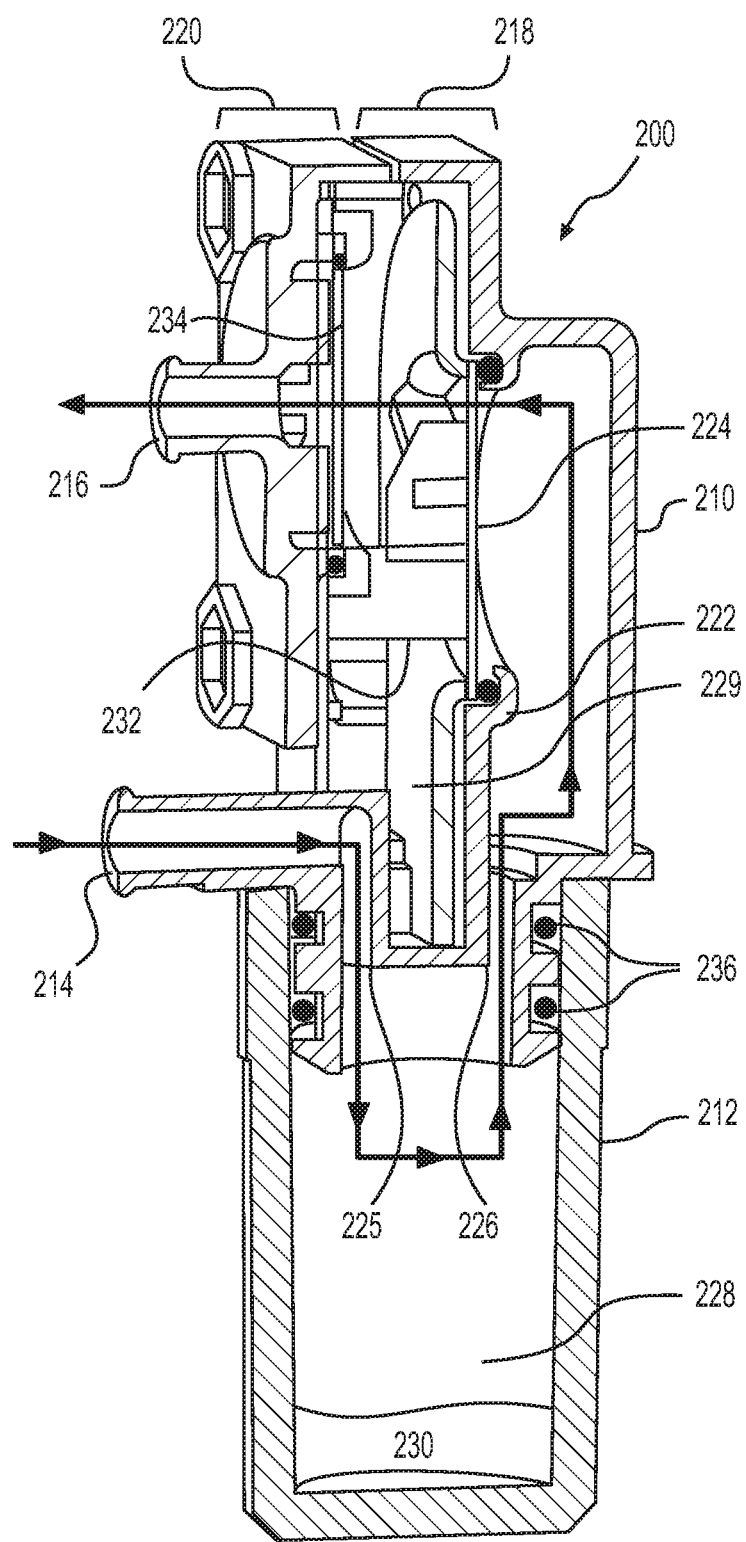
FIG. 2 illustratively depicts a cross section of an exemplary filter assembly according to an exemplary second implementation, in accordance with exemplary embodiments of the present disclosure.
Figure 3:
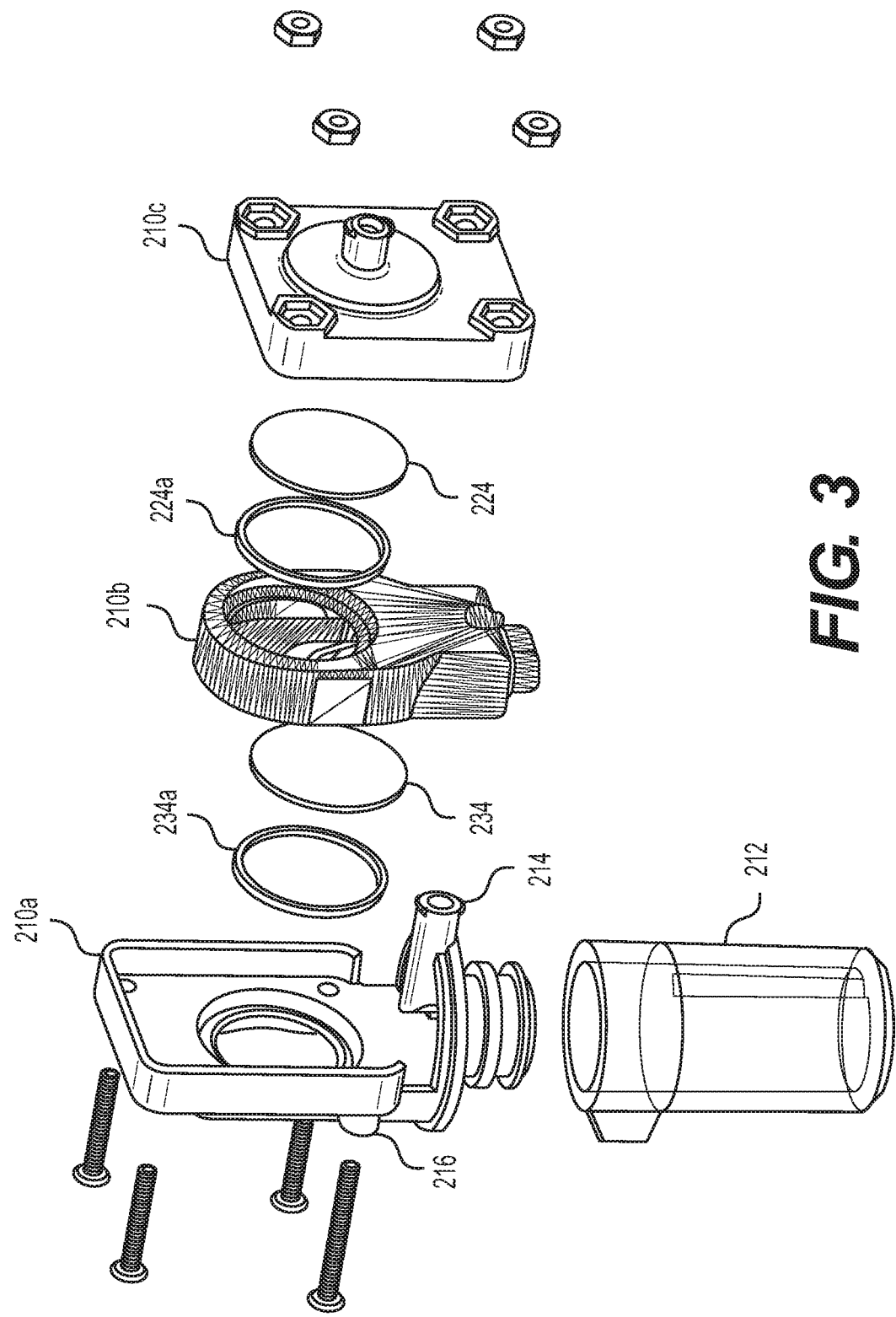
FIG. 3 illustratively depicts an exploded view of the exemplary filter assembly of FIG. 2, in accordance with exemplary embodiments of the present disclosure.

FIGS. 2 and 3 illustratively depict a cross section of a filter assembly 200 according to a second implementation. FIG. 2 illustratively depicts a cross section of a filter assembly 200. FIG. 3 illustratively depicts an exploded view of the filter assembly 200. Some items are common, or interchangeable in this exemplary implementation, with that of FIG. 1, and other implementations. An upper housing 210 is detachably joined with a lower housing 212. The upper housing includes housing portions 212*a,* 212*b,* and 212*c.* The upper housing 210 includes an inlet 214, which receives a flow of gas, which may, for example be sample gas taken from an inspiratory limb or other portion of a breathing gas device, as described in more detail below. The upper housing 210 also includes an outlet 216, from which filtered gas exits the filter assembly 200, and the outlet 216 may be connected to a downstream component of a breathing gas device such as a gas sampling system or gas analyzer, as described in more detail below.

The upper housing 210 may be referred to as housing a "first stage filtration portion" 218, which may also be referred to as a "coalescing filtration portion" 218, and a "second stage filtration portion" 220 which may also be referred to as a "hydrophobic filtration portion 220. The first stage filtration portion supports a coalescing filter media, or filter membrane 224 which may also be referred to as a first stage media 224.

The first stage media 224 may be adapted to remove a range of airborne entrained liquid from the gas. The first stage media 224 may also remove particulate matter. For example the first stage media 224 may, in some examples remove 1.0 micron or larger droplets or particulates. The first stage media 224 may, in some examples have a glass fiber type mesh construction creating a textured surface. The gas first passes through an aperture 225, and a second aperture 226. As the gas passes through the first stage media 224, liquid droplets form in the mesh construction and collect on the textured surface. These droplets are drawn by gravity and/or other forces (e.g., negative pressure, gravity, etc.) to the back, lower side of the first stage media 224 and fall downward off the first stage media 224 as depicted schematically. The droplets may pass through the channel or aperture 226 at a lower end of the upper housing 210, and fall into a collection basin 228, collecting into a pool 230.

The now first-stage-filtered gas is driven, for example, by pressure (e.g., pressure differential) sideways through a into the second stage filtration portion 220. The first stage filtered gas now passes through a hydrophobic filter media 234, or filter membrane 234 which may also be referred to as a second stage media 234.

The second stage media 234 may also be adapted to remove of a range of airborne entrained liquid from the gas, and may to some extent remove 0.2 micron or larger droplets or particulate matter. For example, the second stage media 234 may in some examples be a porous PTFE material. As the gas flows through the second stage media 234 droplets and particulates will be blocked from passing through, and may simply fall via gravity and/or other forces (e.g., negative pressure, gravity, etc.) into a secondary collection basin 229. The gas that has passed through the second stage media 234 then exits the filter assembly 200 via the outlet 216.

It will be noted in this exemplary implementation, that the first stage media 224 may be referred to as being more coarse (less fine) than the second stage media 234. The first stage media 224 may thus be, in some examples, considered a pre-filter for the second stage media 234. In so doing, the first stage media 224 may extend the useful lifespan of the second stage media 234, because the first stage media 224 removes droplets or particles that would effectively clog up or oversaturation, wetting out or blinding occlusion of the second stage media 234.

In this exemplary implementation, both of the first stage media 224 the second stage media 234 is also separated from the pool 230 by a vertical distance and by the size of the aperture 226. These features help avoid the likelihood of liquid in the pool 230 from splashing (e.g., during movement of the filter assembly 200) or evaporating towards the second stage media 234. This degree of enhanced separation of the pool 230 from the second stage media 234 also may extend the useful life of the second stage media 234. The pre-filtration by the first stage media 224 may also have the advantage of reducing the needed area and amount of material for the second stage media 134, compared to if the pre-filtration was not provided. In this variation, the collection basin 229 that collects from the second filter media 234 is a part of the upper housing and keeps separate any drops falling from the second filter media 234, as compared to the lower basin 228 which collects drops falling from the first filter media 224.

The first stage media 224 and second stage media 234 are each mounted at their peripheries to the upper housing 210, so that all gas must pass through both media. This may be accomplished via various mounting and attachment methods such as gluing, mechanical connection into a groove, compression, heat welding, vibration welding, other welding, pre-molding or overmolding into the housing 210, and/or other attachments. For example, sealing rings 224*a* and 234*a* are shown. The media 224 and 234 may have an overmolded outer structural support that is mechanically attached to the housing 210. Gaskets may also be overmolded or placed as part of the attachment to the housing 210. In some implementations, the design may focus on a stricter or tighter surrounding fit for the second stage media 234, since this is the final desired filtration density.

The two stage implementation also provides for a first stage that may, in some implementations and situations, remove mostly water droplets, and a second stage that may primarily remove nebulized liquid such as a drug or saline that may be in the gas entering the filter assembly 200.

The lower housing 212 may be removably, in some implementations, attached to the upper housing 210. This may be a friction fit using elastomeric O-rings 236 as shown in FIG. 1. There may also be threading attaching the lower and upper housings 210 and 212. Removal of the lower housing 212 permits a user to empty the pooled content 230. The lower housing 212 may be transparent or translucent to assist the user in observing when to remove and empty the liquid lower housing 212. In some implementations, the secondary basin 229 may be not need to be emptied during the useful life of the assembly 200, as it may in some situations not collect as much liquid as the lower housing 212.

Figure 4:
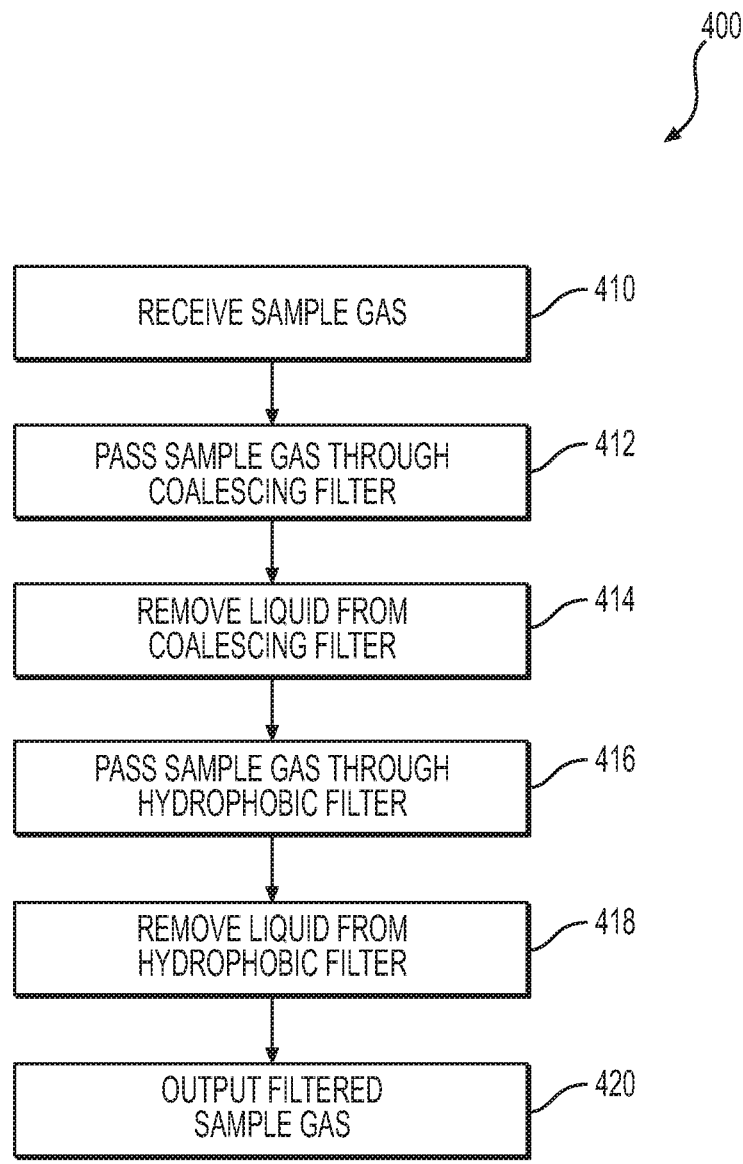
FIG. 4 illustratively depicts an exemplary flow diagram of a method for filtration, in accordance with exemplary embodiments of the present disclosure.

FIG. 4 illustratively depicts an exemplary flow diagram of an exemplary method for filtration, using a filter assembly. At process 410, sample gas is received such as via an inlet at the filter assembly. At process 412, the sample gas is passed through a first stage filter, which may be a coalescing filter as described above. At process 414, liquid is removed from the sample gas by the first stage filter. The removal may be due to collection of droplets that fall via gravity and/or other forces (e.g., negative pressure, gravity, etc.) into a collection basin such as a lower housing described above. Alternatively, the collection basin may be its own basin in the upper housing. At process 416, the sample gas may be passed through a second stage filter, which may be a hydrophic filter as described above. At process 418, liquid is removed from the hydrophobic filter, which may also fall via gravity and/or other forces (e.g., negative pressure, gravity, etc.) into a collection basin, which may be a lower housing as described above.

Figure 5:
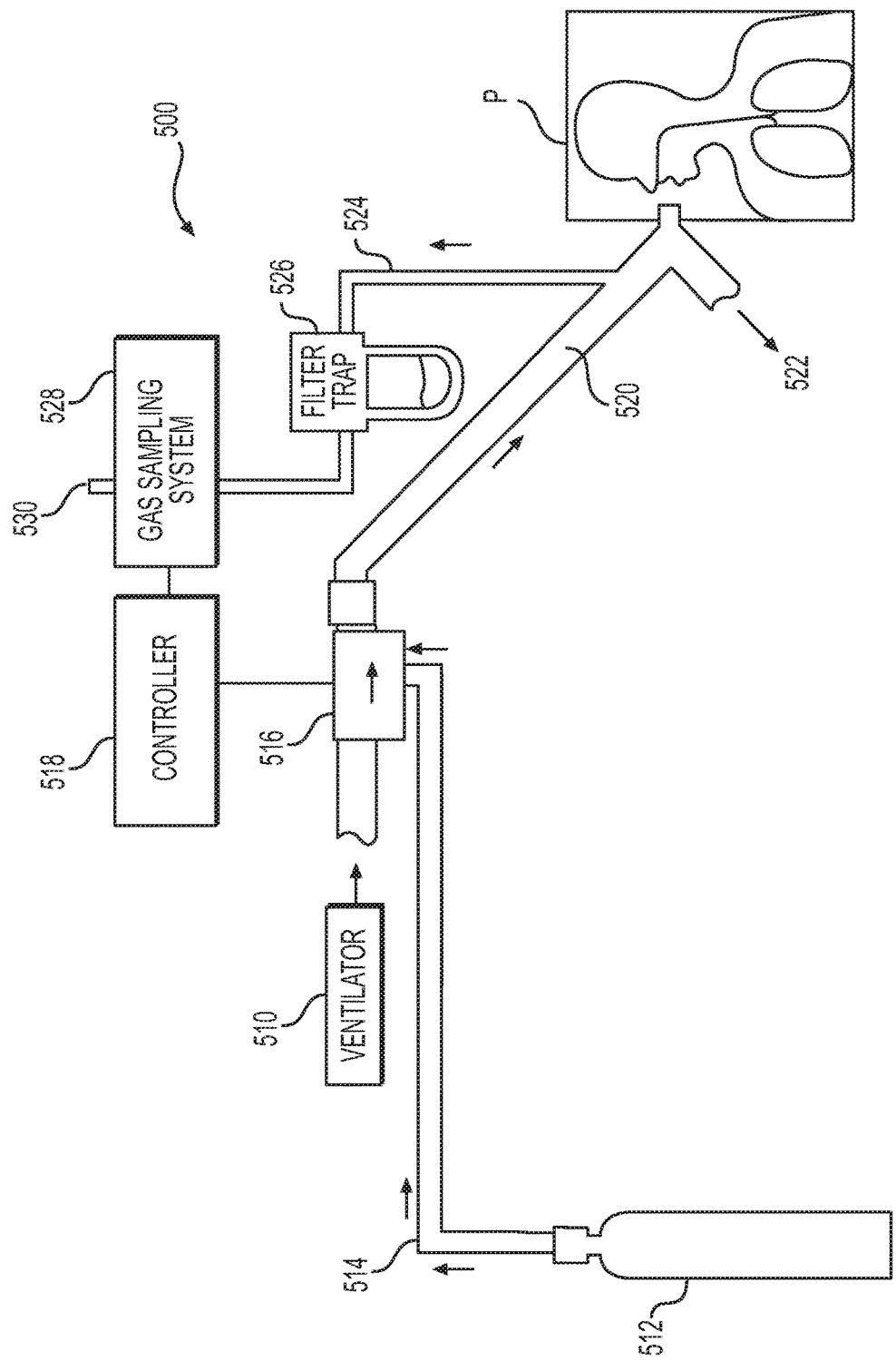
FIG. 5 illustratively depicts at least some aspects of implementation of a filter in conjunction with a breathing gas supply apparatus, in accordance with exemplary embodiments of the present disclosure.

FIG. 5 illustratively depicts some aspects of exemplary implementations of exemplary filters in conjunction with a breathing gas supply apparatus. This exemplary implementation relates to a breathing apparatus, and does not limit the other various implementations of filter assemblies according to this disclosure. An apparatus 500 is used with a ventilator 510. A supply 512 of supplemental or additive gas such as NO provides a supply to conduit 514 and leads to a valve 516 which may also be connected to the ventilator 510. At any stage of breathing gas supply, other additional breathing materials such as nebulized drugs may be provided into a stream that travels via conduit 520. A controller 518 may actuate valves to control the ratio of NO and nebulized drugs to the mixture gas in conduit 520. A patient inhales the content of conduit 520 which may be considered as an inspiratory limb. The patients exhale or excess gas may be considered as an expiratory limb conduit 522.

In this example, a conduit 524 is in fluid communication with the inspiratory limb and may be referred to as a sample gas line. A filter trap 526 receives some or all of the sample gas. This filter trap 526 may correspond to a filter assembly such as described above. After being filtered by the filter trap 526, the gas is passed to a gas sampling system 528, and may exhaust via exhaust outlet 530.

In some examples herein, the sample gas line is connected directly to the water trap assembly. This direct connection can prevent unfiltered sample gas from contacting reusable material with the gas sampling system. The entire water trap assembly may be also disconnectable and in some implementations disposable.

In addition to variations and implementations described herein, the gas analyzer may include a sensor such as a gyroscopic sensor to determine if water and/or other materials are being filtered to a desired degree, and could in some implementations further indicate by sound or visually that the water trap is not properly operating to a desired degree.

It will be appreciated that, among other aspects, the present disclosure in some implementations relates to a filter apparatus for filtering liquid from a gas, the apparatus having a first housing having a gas inlet and a gas outlet; a first filter media disposed in the housing; a second filter media disposed in the housing; and a second housing forming a first collection basin disposed in the flow path between the first filter media and the second filter media, so that a path is defined for the gas flowing from the inlet, through the first filter media, past the collection basin, through the second filter media, and to the outlet. The present disclosure also relates to a method of passing a gas through a coalescing filter media and through a hydrophobic filter media.

The filter assemblies and methods described herein, may in some implementations be useful to filter liquid (and/or particulates) from a sample gas from a patient breathing apparatus for analysis by a gas sampling system. However, other applications for the filter assemblies and methods may arise.

Other implementations are contemplated. For example, in FIGS. 1 through 3, the inlet and the outlet are shown as part of the upper housings. However, in some variations, the inlet and/or the outlet may be provided on the lower housing or basin.

The foregoing detailed descriptions are presented to enable any person skilled in the art to make and use the disclosed subject matter. For purposes of explanation, specific nomenclature is set forth to provide a thorough understanding. However, it will be apparent to one skilled in the art that these specific details are not required to practice the disclosed subject matter. Descriptions of specific applications are provided only as representative examples. Various modifications to the disclosed implementations will be readily apparent to one skilled in the art, and the general principles defined herein may be applied to other implementations and applications without departing from the scope of this disclosure. The sequences of operations described herein are merely examples, and the sequences of operations are not limited to those set forth herein, but may be changed as will be apparent to one of ordinary skill in the art, with the exception of operations necessarily occurring in a certain order. Also, description of functions and constructions that are well known to one of ordinary skill in the art may be omitted for increased clarity and conciseness. This disclosure is not intended to be limited to the implementations shown, but is to be accorded the widest possible scope consistent with the principles and features disclosed herein.

It will be apparent to those skilled in the art that various modifications and variations can be made to the methods and systems of the present description without departing from the spirit and scope of the description. Thus, it is intended that the present description include modifications and variations that are within the scope of the appended claims and their equivalents.

It will be understood that any of the steps described can be rearranged, separated, and/or combined without deviated from the scope of the invention. For ease, steps are, at times, presented sequentially. This is merely for ease and is in no way meant to be a limitation. Further, it will be understood that any of the elements and/or embodiments of the invention described can be rearranged, separated, and/or combined without deviated from the scope of the invention. For ease, various elements are described, at times, separately. This is merely for ease and is in no way meant to be a limitation.

The separation of various system components in the examples described above should not be understood as requiring such separation in all examples, and it should be understood that the described components and systems can generally be integrated together in a single packaged into multiple systems and/or multiple components. It is understood that various modifications may be made therein and that the subject matter disclosed herein may be implemented in various forms and examples, and that the teachings may be applied in numerous applications, only some of which have been described herein. Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A filter apparatus for filtering liquid from a gas, comprising:
   a housing having a gas inlet and a gas outlet;
   a first filter media disposed in the housing;
   a second filter media disposed in the housing; and
   a first collection basin disposed in a flow path between the first filter media and the second filter media,
   wherein a path is defined for enabling the gas to flow from the gas inlet, through the first filter media, past the first collection basin, through the second filter media, and to the gas outlet,
   wherein the first filter media has a pore size that is a larger than a pore size of the second filter media, and
   wherein the first filter media and the second filter media are arranged at a non-zero angle relative to each other.

2. The apparatus of claim 1, wherein the first filter media is a coalescing media.

3. The apparatus of claim 2, wherein the second filter media is a hydrophobic media.

4. The apparatus of claim 1, wherein the second filter media is a hydrophobic media.

5. The apparatus of claim 1, wherein the first filter media and the second filter media are both mounted, respectively, to the housing.

6. The apparatus of claim 1, wherein the first filter media is configured so that droplets of liquid collected by the first filter media may fall via gravity into the first collection basin.

7. The apparatus of claim 6, wherein the second filter media is configured so that droplets of liquid collected by the second filter media may fall via gravity into the first collection basin.

8. The apparatus of claim 1, wherein the second filter media is configured so that droplets of liquid collected by the second filter media may fall via gravity into the first collection basin.

9. The apparatus of claim 1, wherein the first filter media has a filtration density in a range of approximately 1 micron to 5 microns.

10. The apparatus of claim 9, wherein the second filter media has a filtration density in a range of approximately 0.1 microns to 0.2 microns.

11. The apparatus of claim 1, wherein the second filter media has a filtration density in a range of approximately 0.1 micron to 0.2 microns.

12. The apparatus of claim 1, wherein the housing defines a first aperture below the first filter media, and a second aperture below the second filter media, with the first and second apertures sized so that liquid drops fall though the apertures, but splashing from the basin to the second media is inhibited.

13. The apparatus of claim 12, wherein the housing is arranged along a vertical axis during use, and wherein the first and second filter media are each arranged at a respective non-zero angle relative to the vertical axis.

14. The apparatus of claim 1, wherein the first filter media comprises a fiberglass material.

15. The apparatus of claim 14, wherein the second filter media comprises a PTFE material.

16. The apparatus of claim 1, wherein the second filter media comprises a PTFE material.

* * * * *